(12) United States Patent
Kamiya et al.

(10) Patent No.: US 7,485,662 B2
(45) Date of Patent: Feb. 3, 2009

(54) THERAPEUTIC AGENT FOR DIABETES MELLITUS

(75) Inventors: Toshikazu Kamiya, Tsuchiura (JP); Akio Shirai, Koto-ku (JP); Miho Takada, Tsukuba (JP); Fumiko Ogino, Tsukuba (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/549,155

(22) PCT Filed: Mar. 19, 2004

(86) PCT No.: PCT/JP2004/003763

§ 371 (c)(1),
(2), (4) Date: Sep. 15, 2005

(87) PCT Pub. No.: WO2004/083179

PCT Pub. Date: Sep. 30, 2004

(65) Prior Publication Data

US 2006/0173066 A1 Aug. 3, 2006

(30) Foreign Application Priority Data

Mar. 19, 2003 (JP) .............................. 2003-074823

(51) Int. Cl.
*A61K 31/40* (2006.01)
*A61K 31/21* (2006.01)
(52) U.S. Cl. ........................ 514/408; 514/424; 514/506
(58) Field of Classification Search ................. 514/423, 514/403, 532, 533, 537, 408, 424, 506
See application file for complete search history.

(56) References Cited

U.S. PATENT DOCUMENTS 3,932,638 A * 1/1976 Coirre et al. ................. 514/184

FOREIGN PATENT DOCUMENTS

| CA | 2 433 713 | 7/2002 |
| FR | 2797767 | 3/2001 |
| JP | 63-218621 | 9/1988 |
| JP | 06-024977 | 2/1994 |
| JP | 09-104624 | * 4/1997 |
| JP | 2004-091475 | 3/2004 |
| JP | 2004-091476 | 3/2004 |
| WO | 95/27408 | 10/1995 |

OTHER PUBLICATIONS

Mazieres, et al., "Effects of N-Acetyl Hydroxyproline (Oxaceprol) on an Experimental Post-Contusive Model of Osteoarthritis. A Pathological Study" J. Drug. Dev. 1990., vol. 3, No. 3 1990; pp. 135-142.*

Bungard, H. Design of Prodrugs, pp. 7-9, 21-24, Elsevier, Amsterdam, 1985.*

* cited by examiner

*Primary Examiner*—Jennifer M Kim
(74) *Attorney, Agent, or Firm*—Fitzpatrick, Cella, Harper & Scinto

(57) ABSTRACT

An object of the present invention is to provide a therapeutic agent for diabetes mellitus or insulin resistance improving agent, or to provide foods and drinks, food and drink additives, and feeds or feed additives for treating diabetes mellitus or improving insulin diabetes.

In order to achieve such an object, the present invention provides a therapeutic agent for diabetes mellitus and insulin resistance improving agent comprising hydroxyproline, a hydroxyproline derivative or a pharmaceutically acceptable salt thereof or foods and drinks, food and drink additives, feeds or feed additives for treatment of diabetes mellitus or improvement of insulin resistance comprising the same.

1 Claim, No Drawings

THERAPEUTIC AGENT FOR DIABETES MELLITUS

TECHNICAL FIELD

The present invention relates to a therapeutic agent for diabetes mellitus and an insulin resistance improving agent and also to foods and drinks, food and drink additives, feeds and feed additives for treatment of diabetes mellitus or improving insulin resistance.

BACKGROUND ART

As therapeutic agents for diabetes mellitus, those which promote insulin secretion such as sulfonylurea agent and sulfonylamide agent, those which promote insulin resistance such as thiazolidione agent and biguanide agent, those which improve postcibal hyperglycemia such as α-glucosidase inhibitor, and the like have been known, and for the treatment of diabetes mellitus, these agents are used either solely or in combination.

Hydroxyproline widely occurs in nature as a major amino acid component of collagen and its N-acetyl derivative is used as an anti-inflammatory agent. It has also been used as a material for synthesis of various medicaments such as antibiotic substances of carbapenem type, blood pressure depressant, anti-asthma agent, improving agent for peripheral circulation and blood coagulation inhibitor. Further, due to its functional characteristic of having moisturizing property, it has been used for cosmetics as well (*Bioscience and Industry*, 1998, volume 56, no. 1, pages 11 to 16). It has also been used as a food additive for adjustment of quality of taste and improvement in taste of fruit juice, refreshing soft drink and commonly used food or as a material for flavor ("Commentary for Official Formulary of Food Additives", Seventh Edition, published by Hirokawa Shoten, 1998, pages D-1114 to 1115).

With regard to a pharmacological action of hydroxyproline, an action for suppressing aging of the skin and an action for improving skin quality (WO 00/51561; Japanese Published Unexamined Patent Application No. 080321/2002), anti-inflammatory action, anti-rheumatic action, analgesic action and wound-healing action (Japanese Published Unexamined Patent Application No. 337526/1996) have been known, and there has been no report for an action for anti-diabetes mellitus and improving insulin resistance.

In addition, monohydroxylated amino acids have been known to have insulin-like action and/or insulin-sensitivity promoting action (Japanese Translation of PCT International Application No. 508435/2003) but no data concerning efficacy of hydroxyproline and hydroxyproline derivatives have been shown therein at all.

DISCLOSURE OF THE INVENTION

An object of the present invention is to provide a therapeutic agent for diabetes mellitus and an insulin resistance improving agent as well as foods and drinks, food and drink additives, feeds and feed additives for treatment of diabetes mellitus or improving insulin resistance.

The present invention relates to the following (1) to (14).

(1) A therapeutic agent for diabetes mellitus, which comprises as an active ingredient, hydroxyproline or a hydroxyproline derivative represented by the Formula (I) [hereinafter referred to as compound (I)] or a pharmaceutically acceptable salt thereof:

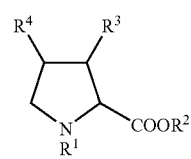

[wherein $R^1$ is hydrogen or acyl; $R^2$ is hydrogen or a saturated or unsaturated hydrocarbon group; and one of $R^3$ and $R^4$ is hydrogen while the other is $OR^5$ (in which $R^5$ is hydrogen or acyl)].

(2) A food and drink or a food and drink additive for the treatment of diabetes mellitus, which comprises the compound (I) or a pharmaceutically acceptable salt thereof as an active ingredient.

(3) A feed or a feed additive for the treatment of diabetes mellitus, which comprises the compound (I) or a pharmaceutically acceptable salt thereof as an active ingredient.

(4) An agent for improvement of insulin resistance, which comprises the compound (I) or a pharmaceutically acceptable salt thereof as an active ingredient.

(5) A food and drink or a food and drink additive for improvement of insulin resistance which comprises the compound (I) or a pharmaceutically acceptable salt thereof as an active ingredient.

(6) A feed or a feed additive for improvement of insulin resistance, which comprises the compound (I) or a pharmaceutically acceptable salt thereof as an active ingredient.

(7) A method for treating diabetes mellitus, which comprises administering the compound (I) or a pharmaceutically acceptable salt thereof.

(8) A method for improving insulin resistance, which comprises administering the compound (I) or a pharmaceutically acceptable salt thereof.

(9) Use, of the compound (I) or a pharmaceutically acceptable salt thereof for the manufacture of a therapeutic agent for diabetes mellitus.

(10) Use of the compound (I) or a pharmaceutically acceptable salt thereof for the manufacture of foods and drinks or food and drink additives for the treatment of diabetes mellitus.

(11) Use of the compound (I) or a pharmaceutically acceptable salt thereof for the manufacture of feeds or feed additives for the treatment of diabetes mellitus.

(12) Use of the compound (I) or a pharmaceutically acceptable salt thereof for the manufacture of an agent for improving insulin resistance.

(13) Use of the compound (I) or a pharmaceutically acceptable salt thereof for the manufacture of foods and drinks or food and drink additives for the improvement of insulin resistance.

(14) Use of the compound (I) or a pharmaceutically acceptable salt thereof for the manufacture of feeds or feed additives for the improvement of insulin resistance.

With regard to the definition for each group in the compound (I), the acyl includes, for example, straight or branched acyl group having 2 to 23 carbon atoms and, specific examples thereof include, for example, acetyl, propionyl, butyryl, isobutyryl, valeryl, hexanoyl, heptanoyl, octanoyl, decanoyl, eicosanoyl, tricosanoyl, etc. Among them, acetyl and propionyl are preferred.

The saturated or unsaturated hydrocarbon group includes, for example, a straight or branched, and saturated or unsaturated hydrocarbon group having 1 to 30 carbon atoms and, specific examples thereof include, for example, methyl, ethyl, propyl, isopropyl, butyl, tert-butyl, isobutyl, 3-methyl-1-butyl, 2-methyl-1-butyl, pentyl, hexyl, octyl, 2-ethylhexyl, lauryl, myristyl, palmityl, stearyl, oleyl, eicosanoyl, phytyl, behenyl, melissyl, triacontyl, etc. Among them, a straight or branched, and saturated or unsaturated hydrocarbon group having 1 to 20 carbon atoms is preferred, and as more specific examples, mention may be made of methyl, ethyl, propyl, isopropyl, butyl, tert-butyl, isobutyl, 3-methyl-1-butyl, 2-methyl-1-butyl, pentyl, hexyl, octyl, 2-ethylhexyl, lauryl, myristyl, palmityl, stearyl, oleyl, eicosyl, phytyl, etc.

The compound (I) in which $R^1$ and $R^2$ are hydrogen and one of $R^3$ and $R^4$ is hydrogen while the other is OH, is hydroxyproline. Hydroxyproline widely occurs in nature as a major amino acid component of collagen and as an amino acid component of elastin. It has been known that there exist eight kinds of stereoisomers of natural hydroxyproline which are distinct from one another, depending on whether proline is the D-form or the L-form, whether the hydroxyl group is at the 3-position or the 4-position, and whether the stereoisomer is the cis-form or the trans-form. Specific examples thereof are mentioned as cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

Although hydroxyproline of any such structure is able to be used in the present invention, trans-4-hydroxy-L-proline is preferably used.

Hydroxyproline is able to be produced by subjecting collagen derived from animals such as pig and cow to acid hydrolysis and purifying the hydrolysate according to a conventional method. However, hydroxyproline produced using microorganisms is preferably used.

Useful microorganisms include those belonging to the genus selected from the group consisting of the genus *Amycolatopsis*, the genus *Dactylosporangium* and the genus *Streptomyces* or those into which a proline 3-hydroxylase gene or a proline 4-hydroxylase gene derived from these microorganisms has been introduced. Introduction of a proline 3-hydroxylase gene or a proline 4-hydroxylase gene derived from a microorganism belonging to the genus selected from the group consisting of the genus *Amycolatopsis,* the genus *Dactylosporangium* and the genus *Streptomyces* into a microorganism can be carried out according to the methods described in Molecular Cloning, A Laboratory Manual, Second Edition, Cold Spring Harbor Laboratory Press (1989), Current Protocols in Molecular Biology, John Wiley & Sons (1987-1997), etc.

Furthermore, trans-4-hydroxy-L-proline is able to be produced using proline 4-hydroxylase isolated from a microorganism belonging to the genus *Amycolatopsis* or the genus *Dactylosporangium* (Japanese Published Unexamined Patent Application No. 313179/1995), and cis-3-hydroxy-L-proline is able to be produced using proline 3-hydroxylase isolated from a microorganism belonging to the genus *Streptomyces* (Japanese Published Unexamined Patent Application No. 322885/1995) [*Bioindustry*, 14, 31 (1997)].

A compound where $R^1$ or $R^2$ is acyl is able to be produced from a compound where $R^1$ or $R^5$ is hydrogen by a known method mentioned, for example, in WO 00/51561, etc.

A compound where $R^2$ is a saturated or unsaturated hydrocarbon group is able to be produced from a compound where $R^2$ is hydrogen by a known method mentioned, for example, in Japanese Published Unexamined Patent Application No. 355531/2000.

When the defined group changes under the condition of the conducted method or is not suitable for conducting the method, an aimed compound is able to be produced by a method for introduction and elimination for protective groups which is commonly used in synthetic organic chemistry [for example, "Protective Groups in Organic Synthesis" by T. W. Greene, published by John Wiley & Sons, Inc. (1981)] and the like.

The resulting compound is able to be purified by a common purifying method such as crystallization and chromatography.

As the pharmaceutically acceptable salt of the compound (I), mention may be made of alkali metal salts such as sodium salts, potassium salts, etc., alkaline earth metal salts such as magnesium salts, calcium salts, etc., ammonium salts such as ammonium, tetramethylammonium, etc., organic amine addition salts to which morpholine, piperidine, etc. and the like.

The therapeutic agent for diabetes mellitus or the insulin resistance improving agent of the present invention is a pharmaceutical preparation comprising, as an active ingredient, the compound (I) or a salt thereof either solely or in a mixed state or as a mixture with other ingredients for any other treatment.

Such a pharmaceutical preparation is able to be prepared by mixing the active ingredient with one or more pharmaceutically acceptable carriers followed by subjecting to any method which has been well known in the technical field of pharmaceutical preparations.

In administering the preparation, it is desirable to select a route of administration that is the most effective in the treatment and its examples are oral administration and parenteral administrations such as intravenous, intraperitoneal or subcutaneous administration, and an oral administration is preferred.

With regard to the dosage form, any of oral preparation such as tablets, diluted powder, granules, pill, suspensions, emulsion, infusion/decoction, capsules, syrup, liquid, elixir, extract, tincture, fluid extract, etc. and parenteral preparation such as injection, drip infusion, cream, suppository, etc. may be used and an oral preparation is preferably used.

In the manufacture of an oral preparation, it is possible to use additives such as excipient, binder, disintegrating agent, lubricant, dispersing agent, suspending agent, emulsifier, diluting agent, buffer, antioxidant and cell suppressor.

A liquid preparation such syrup which is appropriate for oral administration is able to be prepared by addition of water, saccharide such as sucrose, sorbitol, fructose, etc., glycol such as polyethylene glycol, propylene glycol, etc., oil such as sesame oil, olive oil, soybean oil, etc., antiseptic such as p-hydroxybenzoate, etc., preservative such as p-hydroxybenzoate derivatives (e.g., methyl p-hydroxybenzoate), sodium benzoate, etc., flavor such as strawberry flavor, peppermint, etc. and the like.

Tablets, powder, granule, etc. which are suitable for oral administration are able to be prepared by addition of saccharide such as lactose, sugar, glucose, sucrose, mannitol, sorbitol, etc., starch such as potato, wheat, corn, etc., inorganic substance such as calcium carbonate, calcium sulfate, sodium hydrogen carbonate, sodium chloride, etc., excipient such as crystalline cellulose, plant powder (e.g., powdered licorice and powdered gentian), etc., disintegrating agent such as starch, agar, powdered gelatin, crystalline cellulose, carmellose sodium, carmellose calcium, calcium carbonate, sodium hydrogen carbonate, sodium alginate, etc., lubricant such as magnesium stearate, talc, hydrogenated plant oil, Macrogol, silicone oil, etc., bonding agent such as polyvinyl alcohol, hydroxypropyl cellulose, methyl cellulose, ethyl cellulose, carmellose, gelatin, starch paste, etc., surfactant such as fatty acid ester, etc., plasticizer such as glycerol, and the like.

Preparation suitable for parenteral administration such as an injection preparation preferably comprises a sterilized aqueous preparation which is isotonic to blood of the person to be administered containing a compound (I) or a salt thereof. For example, in the case of an injection preparation, a solution for injection is prepared using a salt solution, a glucose solution or a carrier comprising a mixture of a salt solution and a glucose solution and the like.

In such a parenteral preparation, it is also possible to add one or more auxiliary component (s) selected from diluent, antiseptic agent, flavor, excipient, lubricant, bonding agent, surfactant, plasticizer, etc. which were exemplified for an oral preparation already.

The dose and the administering frequency of the preparation of the present invention vary depending upon dosage form and age, body weight, nature of symptom to be treated or degree of severeness of a patient and, usually, the preparation is administered once to several times a day so that the dose as the compound (I) or a salt thereof is made 5 mg to 5,000 mg or, preferably, 50 mg to 5,000 mg a day for an adult.

Although there is no particular limitation for the administering period, it is usually from 1 day to 1 year and, preferably, from 2 weeks to 3 months.

The preparation of the present invention is able to be used not only to human being but also to animals except human being (hereinafter, abbreviated as non-human animals).

As the non-human animals, mention may be made of mammals, birds, reptiles, amphibians, fish and animals other than human being.

The dose in the case of administration to non-human animals varies depending upon age and type of the animal and nature or degree of severeness of symptom and, usually, the preparation is administered once to several times a day so that the dose as the compound (I) or a salt thereof is made 0.5 mg to 500 mg or, preferably, 5 mg to 500 mg a day per kg of body weight.

Although there is no particular limitation for the administering period, it is usually from 1 day to 1 year and, preferably, from 2 weeks to 3 months.

By the same method as in the case of the preparation of the present invention, it is possible to prepare a food and drink additives comprising the compound (I) or a salt thereof as an active ingredient.

If necessary, other food and drink additives is mixed with and dissolved in the food and drink additives of the present invention whereupon it is possible to make into the form of, for example, powder, granules, pellets, tablets and various liquid preparations.

The foods and drinks of the present invention are able to be processed and manufactured by the conventional method for the manufacture of foods and drinks except that the compound (I) or a salt thereof or a food and drink additive of the present invention is added to foods and drinks.

The foods and drinks of the present invention are also able to be produced by using granulating methods such as fluidized bed granulation, stirring granulation, extrusion granulation, rolling granulation, air stream granulation, compression molding granulation, disruption granulation, spray granulation and blasting granulation, coating methods such as pan coating, fluidized bed coating and dry coating, plumping methods such as puff drying, excess steam method, foam mat method and microwave heating method, and extrusion methods using an extruding granulator or an extruder.

The foods and drinks of the present invention may be in any of the forms including juice, refreshing soft drinks, tea, lactic acid beverages, dairy products such as fermented milk, frozen dessert, butter, cheese, yogurt, processed milk and skim milk, meat products such as ham, sausages and hamburger, fish products such as steamed, baked or fried fish paste, egg products such as baked or steamed foods made of beaten eggs, confectionery such as cookies, jellies, chewing gum, candies and snacks, bread, noodles, pickles, smoked foods, dried fish, preserved foods boiled down in soy sauce, salted foods, soups, seasonings, etc.

Furthermore, the foods and drinks of the present invention may take the form of a powdered food, a sheet-shaped food, a bottled food, a canned food, a retort food, a capsule food, a tablet food, a liquid food, a health drink, etc.

The foods and drinks of the present invention are able to be used as a health food and drink or a functional food and drink having an activity for anti-diabetes mellitus, or an effect for improving insulin resistance.

To the foods and drinks or food and drink additives of the present invention may be added food additives which are commonly used in foods and drinks such as sweeteners, coloring agents, preservatives, thickening stabilizers, antioxidants, color developing agents, bleaching agents, fungicides, gum bases, battering agents, enzymes, glazing agents, acidulants, seasonings, emulsifiers, nutrient supplements, additional materials for preparation, flavors, spice extracts, etc. which are mentioned, for example, in "Handbook for Indication of Food Additives" (Japan Food Additives Association, published on Jan. 6, 1997).

Adding amount of the compound (I) or a salt thereof or of the food and drink additives to the foods and drinks of the present invention may be appropriately selected depending upon the type of foods and drinks, effect expected by ingestion of said foods and drinks, etc. and, usually, it is added so as to contain 0.1% by weight to 100% by weight or, preferably, 1.0% by weight to 100% by weight therein as the compound (I) or a salt thereof.

Depending upon ingestion form, age and body weight of a person to whom it is ingested, etc., the foods and drinks of the present invention is orally administered or, in other words, ingested once to several times a day so that amount as the compound (I) or a salt thereof is made 5 mg to 5,000 mg or, preferably, 50 mg to 5,000 mg a day to an adult.

Although there is no particular limitation for the ingesting period, it is usually from 1 day to 1 year, preferably, from 2 weeks to 3 months.

By the same method as in the case of the food and drink additives of the present invention, it is possible to prepare a feed additive comprising the compound (I) or a salt thereof as an active ingredient. If necessary, other feed additive is mixed with and dissolved in the feed additives of the present invention whereupon it is possible to make into the form of, for example, powder, granules, pellets, tablets and various liquid preparations.

The feed of the present invention is able to be processed and manufactured by the conventional method for the manufacture of feed except that the compound (I) or a salt thereof or a feed additive of the present invention is added to feed for non-human animals.

The feed for non-human animals include any feed for non-human feed for mammals, birds, reptiles, amphibians, fish, etc. and its examples include feed for pets such as dogs, cats, mice, etc., feed for livestock such as cows, pigs, etc., feed for poultry such as hens, turk, etc. and feed for cultivated fish such as sea breams, young yellowtails, etc., and the like.

Examples of the feed to which the compound (I) or a salt thereof or the feed additive of the present invention is to be added include cereals, chaff and bran, vegetable oil cakes, animal-based feed materials, other feed materials, purified products thereof, etc.

As the cereals, mention may be made of milo, wheat, barley, oats, rye, brown rice, buckwheat, foxtail millet, broomcorn millet, Japanese millet, corn, soybean, etc.

As the chaff and bran, mention may be made of rice bran, defatted rice bran, wheat bran, wheat middlings, wheat germ, barley bran, pellet, corn bran, corn germ, etc.

As the vegetable oil cakes, mention may be made of soybean oil cake, soybean flour, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake, etc.

As the animal-based feed materials, mention may be made of fish powder (such as northern ocean meal, imported meal, whole meal and coastal meal), fish soluble, meat powder, meat and bone powder, blood powder, degraded hair, bone powder, treated by-products for livestock, feather meal, silkworm pupa, skim milk, casein, dry whey, etc.

As other feed materials, mention may be made of stalks and leaves of plants (such as alfalfa, hay cube, alfalfa leaf meal, powder of false acacia, etc.), by-products from the corn processing industry (such as corn gluten meal, corn gluten feed, corn steep liquor, etc.), processed starch products (such as starch, etc.), sugar, products from the fermentation industry (such as yeast, beer cake, malt root, alcohol cake, soy sauce cake, etc.), agricultural by-products (such as processed citrus fruit cake, tofu cake, coffee cake, cocoa cake, etc.), cassava, broad bean, guar meal, seaweeds, krill, spirulina, chlorella, minerals, etc.

As the purified products thereof, mention may be made of proteins (such as casein, albumin, etc.), amino acids, saccharides (such as starch, cellulose, sucrose, glucose, etc.), minerals, vitamins, etc.

The feed of the present invention is also to be produced by using granulating methods such as fluidized bed granulation, stirring granulation, extrusion granulation, tumbling granulation, air stream granulation, compression molding granulation, disruption granulation, spray granulation and blasting granulation, coating methods such as pan coating, fluidized bed coating and dry coating, plumping methods such as puff drying, excess steam method, foam mat method and microwave heating method and extrusion methods using an extruding granulator or an extruder.

The feed of the present invention is able to be used as a feed for anti-diabetes mellitus or improving insulin resistance.

Adding amount of the compound (I) or a salt thereof or of the feed additive to the feed of the present invention may be appropriately selected depending upon the type of feed, effect expected by ingestion of said feed, etc. and, usually, it is added so as to contain 0.1% by weight to 100% by weight or, preferably, 1.0% by weight to 100% by weight therein as the compound (I) or a salt thereof.

When the feed of the present invention is ingested to non-human animals, depending upon ingestion form, type of the ingesting animals, age and body weight of the animal, etc., the feed is orally administered or, in other words, ingested once to several times a day so that amount as the compound (I) or a salt thereof is made 0.5 mg to 500 mg or, preferably, 5 mg to 500 mg a day to an adult.

Although there is no particular limitation for the ingesting period, it is usually from 1 day to 1 year and, preferably, from 2 weeks to 3 months.

When the compound (I) or a salt thereof is administered to human being or non-human animals by the above-mentioned method, it is possible to treat diabetes mellitus or improve insulin resistance in the human being or non-human animals.

BEST MODE FOR CARRYING OUT THE INVENTION

EXAMPLE 1

KK-Ay/Ta Jcl mice (Clea Japan, Inc.; male; six weeks age) (15 mice) of a type 2 diabetic model were divided into three groups each comprising five mice and named group 1 to group 3.

The mice of the groups 1 to 3 were made free to take feed and water. A commercially available feed CE-2 (manufactured by Clea Japan, Inc.) was ingested to the mice of group 1. CE-2 to which 1% by weight of trans-4-hydroxy-L-proline (manufactured by Kyowa Hakko Kogyo; hereinafter, abbreviated as hydroxyproline) was added was ingested to the mice of group 2. CE-2 to which 1% by weight of trans-N-acetyl-4-hydroxy-L-proline (manufactured by Kyowa Hakko Kogyo; hereinafter, abbreviated as N-acetylhydroxyproline) was added was ingested to the mice of group 3.

On the initial day of the test and on the 17th day thereafter, blood was collected from tail vein and blood-sugar level upon non-fasting was measured by a Medisafe Reader GR-101 (manufactured by Thermo Co.). The mice were fasted for 18 hours during the 17th day to the 18th day after the start of the test and whole blood was collected from descending vena cava to prepare serum. The serum-insulin level was measured by a Levi Insulin Kit Mouse-T (manufactured by Shibayagi). The value was shown by mean value±standard error (n=5) and statistic ratio of risk (p value) was determined by a t-test. With regard to the ingested amounts during the test periods, there was no significant difference among the groups 1 to 3.

Results of measurement of blood-sugar levels upon non-fasting on the initial day of the test and on the 17th day thereafter are shown in Table 1.

TABLE 1

| | Blood-Sugar Level (mg/dl) | |
|---|---|---|
| | Initial Day of the Test | 17th Day of the Test |
| Group 1 | 241.3 ± 14.1 | 485.2 ± 27.2 |
| Group 2 | 243.0 ± 12.2 | 260.4 ± 10.8* |
| Group 3 | 241.0 ± 15.5 | 226.2 ± 12.9* |

(*p < 0.0005, to Group 1)

It is apparent from Table 1 that, as compared with the blood-sugar level of the group 1 on the same day, blood-sugar levels in the groups 2 and 3 on the 17th day of the test were significantly low. Thus, in both groups, progress of symptom of hyperglycemia from the initial day of the test was suppressed. From the above result, it is apparent that the hydroxyproline and the N-acetylhydroxyproline have an antidiabetic action.

Results of the measurement of serum-insulin levels are shown in Table 2.

TABLE 2

| | Serum-Insulin Level (ng/ml) |
|---|---|
| Group 1 | 1.11 ± 0.08 |
| Group 2 | 1.01 ± 0.08 |
| Group 3 | 0.69 ± 0.06* |

(*p < 0.005, to Group 1)

It is apparent from Table 2 that, as compared with the serum-insulin level of the group 1, serum-level of the group 3 was significantly low and heperinsulinism was improved. In the serum-insulin level of the group 2, no significant difference was noted as compared with the serum-insulin level of the group 1.

From the results of Table 1 and Table 2, it is apparent that the hydroxyproline and the N-acetylhydroxyproline show an antidiabetic action by improving the insulin resistance.

EXAMPLE 2

KK-Ay/Ta Jcl mice (Clea Japan, Inc.; male;,six weeks age) (15 mice) of a type 2 diabetic model were divided into three groups each comprising five mice and named group 1 to group 3.

The mice of the groups 1 to 3 were made free to take feed and water. A commercially available feed CE-2 (manufactured by Clea Japan, Inc.) was ingested to the mice of group 1. CE-2 to which 1% by weight of trans-4-hydroxy-L-proline ethyl ester (manufactured by Sanyo Chemical Laboratory Co., Ltd.; hereinafter, abbreviated as hydroxyproline ethyl ester) was added was ingested to the mice of group 2. CE-2 to which 1% by weight of trans-N,O-diacetyl-4-hydroxy-L-proline oleyl ester (manufactured by Nissei Kagaku; hereinafter, abbreviated as diacetylhydroxyproline oleyl ester) was added was ingested to the mice of group 3.

On the initial day of the test and on the 10th day thereafter, blood was collected from tail vein and blood-sugar level upon non-fasting was measured by a Medisafe Reader GR-101. The mice were fasted for 18 hours during the 10th day to the 11th day after the start of the test and whole blood was collected from descending vena cava to prepare serum. The serum-insulin level was measured by a Levi Insulin Kit Mouse-T. The value was shown by mean value±standard error (n=5) and statistic ratio of risk (p value) was determined by a t-test. With regard to the ingested amounts during the test periods, there was no significant difference among the groups 1 to 3.

Results of measurement of blood-sugar levels upon non-fasting on the initial day of the test and on the 10th day thereafter are shown in Table 3.

TABLE 3

| | Blood-Sugar Level (mg/dl) | |
|---|---|---|
| | Initial Day of the Test | 10th Day of the Test |
| Group 1 | 252.0 ± 31.6 | 350.4 ± 30.7 |
| Group 2 | 253.0 ± 9.5 | 217.2 ± 11.3* |
| Group 3 | 241.0 ± 11.0 | 215.2 ± 20.3* |

(*p < 0.005, to Group 1)

It is apparent from Table 3 that, as compared with the blood-sugar level of the group 1 on the same day, blood-sugar levels in the groups 2 and 3 on the 10th day of the test were significantly low, and even when compared with the blood-sugar level of the initial day for each of them, the values were low. From the above result, an antidiabetic action of the hydroxyproline ethyl ester and the diacetylhydroxyproline oleyl ester is now apparent.

Results of measurement of serum-insulin levels are shown in Table 4.

TABLE 4

| | Serum-Insulin Level (ng/ml) |
|---|---|
| Group 1 | 0.63 ± 0.02 |
| Group 2 | 0.52 ± 0.10 |
| Group 3 | 0.64 ± 0.12 |

It is apparent from Table 4 that, as compared with the serum-insulin level of the group 1, serum-insulin levels in the groups 2 and 3 showed no significant difference.

From the results of Table 3 and Table 4, it is apparent that the hydroxyproline ethyl ester and the diacetylhydroxyproline oleyl ester show an antidiabetic action by improving the insulin resistance.

EXAMPLE 3

KK-Ay/Ta Jcl mice (Clea Japan, Inc.; male; six weeks age) (16 mice) of a type 2 diabetic model were divided into 2 groups each comprising 8 mice and named group 1 and group 2.

After fasting for 18 hours, a physiological saline solution was orally administered to the mice of the group 1 while, to the mice of the group 2, 1 g/kg body weight (hereinafter, referred to as "B.W.") of a 20% (w/v) aqueous solution of the N-acetylhydroxyproline (dissolved in a physiological saline solution) was orally administered. After 1 hour, 2 g/kg B.W. of a 40% (w/v) aqueous solution of glucose was orally administered to the mice of the groups 1 and 2 to load with sugar. Blood was collected from tail vein 60 minutes before (−60 minutes) administration of the aqueous glucose solution, upon the administration (0 minute) and 30 and 120 minutes after the administration and blood-sugar levels were measured by a Medisafe Reader GR-101. The value was shown by mean value±standard error (n=8) and statistic ratio of risk (p value) was determined by a t-test.

Results of measurement of blood-sugar levels are shown in Table 5.

TABLE 5

| | Blood-Sugar Level (mg/dl) | | | |
|---|---|---|---|---|
| | −60 min | 0 min | 30 min | 120 min |
| Group 1 | 160.2 ± 12.6 | 179.7 ± 12.6 | 490.4 ± 21.2 | 270.9 ± 37.6 |
| Group 2 | 159.4 ± 5.6 | 179.9 ± 11.6 | 407.1 ± 17.1* | 210.4 ± 14.4 |

(*p < 0.05, to the group 1)

It is apparent from Table 5 that, as compared with those of the group 1, after 30 minutes and 120 minutes from administration of an aqueous glucose solution, blood-sugar levels of the group 2 showed lower values and an increase in blood-sugar level by load with sugar was suppressed in the group 2. As a result, an antidiabetic action of the N-acetylhydroxyproline is apparent.

EXAMPLE 4

GK/Jcl rats (Clea Japan, Inc; male; nine weeks age) (12 mice) of a type 2 diabetic model were divided into two groups each comprising six mice and named group 1 and group 2.

Five ml/kg B.W. of a solvent (0.5% (w/v) methyl cellulose #400) was orally administered to the rats of the group 1. A 200 mg/ml solution of the hydroxyproline in the same solvent was orally administered to the rats of the group 2 so as to make the amount of administration 1,000 mg/kg B.W. Blood was collected from tail vein upon administration of the solvent or the hydroxyproline solution (0 minute) and 30 minutes, 60 minutes and 120 minutes after the administration and blood-sugar levels were measured by a Medisafe Reader GR-101. The value was shown by mean value±standard error (n=6) and statistic ratio of risk (p value) was determined by a t-test.

Results of measurement of blood-sugar levels are shown in Table 6.

TABLE 6

| | Blood-Sugar Level (mg/dl) | | | |
|---|---|---|---|---|
| | 0 min | 30 min | 60 min | 120 min |
| Group 1 | 189.7 ± 8.4 | 249.5 ± 9.3 | 249.5 ± 11.6 | 186.3 ± 9.1 |
| Group 2 | 189.2 ± 8.4 | 220.3 ± 13.8 | 189.5 ± 10.9** | 156.0 ± 6.8* |

(*p < 0.05, **p < 0.01, to the group 1)

It is apparent from Table 6 that, as compared with those of the group 1, after 60 minutes and 120 minutes from the administration, blood-sugar levels of the group 2 were significantly low. As a result, an antidiabetic action of the hydroxyproline is apparent.

EXAMPLE 5

GK/Jcl rats (Clea Japan, Inc.; male; nine weeks age) (18 mice) of a type 2 diabetic model were divided into three groups each comprising six mice and named groups 1 to 3.

After fasting for 18 hours, 5 ml/kg B.W. of a solvent (0.5% (w/v) methyl cellulose #400) was orally administered to the rats of the group 1. A 60 mg/ml solution of the hydroxyproline in the same solvent was orally administered to the rats of the group 2 so as to make the amount of administration 300 mg/kg B.W. A 200 mg/ml solution of the hydroxyproline in the same solvent was orally administered to the rats of the group 3 so as to make the amount of administration 1,000 mg/kg B.W. After 30 minutes from the oral administration, 2 g/kg B.W. of a 20% (w/v) aqueous solution of glucose was orally administered to the mice of the groups 1 to 3 to load with sugar. Blood was collected from tail vein 30 minutes before the administration of the aqueous glucose solution (–30 minutes), upon the administration (0 minute) and 30 minutes, 60 minutes and 120 minutes after the administration and blood-sugar levels were measured by a Medisafe Reader GR-101.

The value was shown by mean value±standard error (n =6) and statistic ratio of risk (p value) between the groups 1 and 2 and that between the groups 1 and 3 was determined by a one-way layout dispersion analysis and by a Dunnett test.

Results of measurement of blood-sugar levels are shown in Table 7.

TABLE 7

| | Blood-Sugar Level (mg/dl) | | | | |
|---|---|---|---|---|---|
| | –30 min | 0 min | 30 min | 60 min | 120 min |
| Group 1 | 110.3 ± 3.2 | 141.0 ± 4.2 | 296.8 ± 2.8 | 336.7 ± 9.5 | 211.5 ± 3.8 |
| Group 2 | 113.3 ± 2.7 | 144.2 ± 7.2 | 269.5 ± 15.3 | 298.2 ± 7.5* | 207.5 ± 6.3 |
| Group 3 | 112.2 ± 3.3 | 137.0 ± 6.6 | 226.2 ± 3.0* | 247.3 ± 4.4* | 181.2 ± 7.3* |

(*p < 0.01, to the group 1)

It is apparent from Table 7 that, as compared with that of the group 1, after 60 minutes from the administration of glucose, blood-sugar level of the group 2 was significantly low, and in the group 2, an increase in blood-sugar level by load with sugar was suppressed. After 30, 60 and 120 minutes from the administration of glucose, blood-sugar levels of the group 3 were significantly low compared with those of the group 1 whereby, in the group 3, an increase in blood-sugar level by load with sugar was suppressed. From those results, a dose-dependent antidiabetic-action of the hydroxyproline was apparent.

EXAMPLE 6

Each $1.2 \times 10^5$ C2C12 cells (cell strain derived from striated muscles of mouse; Dainippon Pharmaceutical Co., Ltd.) was inoculated on a 12-well plate and incubated at 37° C. for 3 days in a $CO_2$ incubator (5% $CO_2$/95% air) with a DMEM medium (manufactured by Invitrogen) to which 10% fetal bovine serum (manufactured by Invitrogen) was added. When the cells became confluent, the medium was exchanged to a DMEM medium to which 2% horse serum (manufactured by Invitrogen) was added and incubation was further conducted for 4 days to differentiate to myotubes. The medium was exchanged once again with a DMEM medium to which 2% horse serum was added and further incubated for 3 days after addition of bovine insulin (manufactured by Invitrogen) so as to make its final concentration 1 μg/ml or 0.1 μg/ml, a mixture of bovine insulin and trans-4-hydroxy-L-proline methyl ester (manufactured by Kokusan Chemical Co., Ltd.; hereinafter, referred to as hydroxyproline methyl ester) so as to make their final concentrations 0.1 μg/ml and 100 μg/ml, respectively or a mixture of bovine insulin and hydroxyproline ethyl ester so as to make their final concentrations 0.1 μg/ml and 100 μg/ml, respectively. Each of the supernatant liquids after the incubation was recovered and glucose concentration was measured by a Glucose CII Test Wako (manufactured by Wako Pure Chemical Industries, Ltd.) whereby consumption of glucose of the differentiated C2C12 cells was investigated. The values are shown by mean value±standard deviation (n=3, mg/l) and statistic ratio of risk (p value) was determined by a t-test.

Concentrations of insulin, the hydroxyproline methyl ester and the hydroxyproline ethyl ester added thereto and glucose concentrations in the supernatant liquids after incubation are shown in Table 8.

TABLE 8

| Additives | Glucose (mg/l) |
|---|---|
| (nothing added) | 1859 ± 20 |
| Insulin (0.1 μg/ml) | 1260 ± 15*[1] |
| Insulin (0.1 μg/ml) + hydroxyproline methyl ester (100 μg/ml) | 926 ± 47*[2] |

TABLE 8-continued

| Additives | Glucose (mg/l) |
|---|---|
| Insulin (0.1 μg/ml) + hydroxyproline ethyl ester (100 μg/ml) | 984 ± 29*[2] |
| Insulin (1 μg/ml) | 942 ± 34*[2] |

*[1]$p < 0.001$, to "nothing added"
*[2]$p < 0.005$, to "insulin (0.1 μg/ml)"

It is apparent from Table 8 that, consumption of glucose of C2C12 cells was significantly promoted by addition of 0.1 μg/ml of insulin. Further, in the co-presence of 0.1 μg/ml of insulin and 100 μg/ml of the hydroxyproline methyl ester or 0.1 μg/ml of insulin and 100 μg/ml of the hydroxyproline ethyl ester, the consumption significantly increased to such an extent that, if insulin is used solely, the concentration of as much as ten-fold (1 μg/ml) is necessary to achieve the same result.

From the above results, it is now apparent that the hydroxyproline methyl ester and the hydroxyproline ethyl ester potentiate the action of insulin to the muscle.

EXAMPLE 7

Water was added to a composition having the following formulation mentioned in Table 9 to make 1,000 ml whereupon a refreshing soft drink (for ten bottles) for treatment of diabetes mellitus was prepared.

TABLE 9

| Composition | Amount |
|---|---|
| Hydroxyproline | 5 g |
| Vitamin C | 1 g |
| Vitamin $B_1$ | 5 mg |
| Vitamin $B_2$ | 10 mg |
| Vitamin $B_6$ | 25 mg |
| Liquid Sugar | 150 g |
| Citric Acid | 3 g |
| Flavor | 1 g |

EXAMPLE 8

A composition having the formulation mentioned in Table 10 was extracted with 1,000 ml of water to prepare 1,000 ml of tea beverage for treatment of diabetes mellitus.

TABLE 10

| Composition | Amount |
|---|---|
| Hydroxyproline | 5 g |
| Tea Leaves | 15 g |

EXAMPLE 9

According to the formulation mentioned in Table 11, chewing gum (for 30 pieces) for treatment of diabetes mellitus was prepared.

TABLE 11

| Composition | Amount |
|---|---|
| Hydroxyproline | 1.5 g |
| Gum Base | 25 g |
| Sugar | 63 mg |
| Starch Syrup | 10 mg |
| Flavor | 1 mg |

EXAMPLE 10

According to the formulation mentioned in Table 12, candy (for 20 products) for treatment of diabetes mellitus was prepared.

TABLE 12

| Composition | Amount |
|---|---|
| Hydroxyproline | 1 g |
| Sugar | 80 g |
| Starch Syrup | 20 g |
| Flavor | 0.1 g |

EXAMPLE 11

According to the formulation mentioned in Table 13, tablets (200 mg per tablet) for treatment of diabetes mellitus were prepared by a conventional method.

TABLE 7

| Composition | Amount |
|---|---|
| N-Acetylhydroxyproline | 50 mg |
| Lactose | 90 mg |
| Corn Starch | 30 mg |
| Synthetic Aluminum Silicate | 12 mg |
| Carboxymethylcellulose Calcium | 15 mg |
| Magnesium Stearate | 3 mg |

EXAMPLE 12

According to the formulation mentioned in Table 14, a powder (550 mg per chartula) for treatment of diabetes mellitus was prepared.

TABLE 14

| Composition | Amount |
|---|---|
| Hydroxyproline Methyl Ester | 50 mg |
| Lactose | 300 mg |
| Corn Starch | 200 mg |

EXAMPLE 13

According to the formulation mentioned in Table 15, a hard capsule preparation (160 mg per capsule) for treatment of diabetes mellitus was prepared.

TABLE 15

| Composition | Amount |
| --- | --- |
| Hydroxyproline Methyl Ester | 50 mg |
| Lactose | 60 mg |
| Corn Starch | 30 mg |
| Hydroxypropyl Cellulose | 20 mg |

To 50 mg of hydroxyproline ethyl ester were added 60 mg of lactose and 30 mg of corn starch, and mixing was carried out. An aqueous solution of 20 mg of hydroxypropyl cellulose was added thereto and the mixture was kneaded. Then, granules were prepared using an extruding granulator. The granules were filled in gelatin hard capsules to prepare a hard capsule preparation.

EXAMPLE 14

According to the formulation mentioned in Table 16, a soft capsule preparation (170 mg per capsule) for treatment of diabetes mellitus was prepared.

TABLE 16

| Composition | Amount |
| --- | --- |
| Diacetylhydroxyproline Oleyl Ester | 50 mg |
| Soybean Oil | 120 mg |

To 120 mg of soybean oil was added 50 mg of diacetylhydroxyproline oleyl ester, and mixing was carried out. Then, the mixture was filled in soft capsules using an automated molding machine of a rotary dies type by a conventional method whereupon a soft capsule preparation was prepared.

INDUSTRIAL APPLICABILITY

In accordance with the present invention, there is provided a therapeutic agent for diabetes mellitus or an insulin resistance improving agent, or a food and drink, a food and drink additive, a feed or a feed additive for treatment of diabetes mellitus or improvement of insulin resistance.

The invention claimed is:

1. A method for improving insulin resistance comprising administering, to a patient in need thereof, an effective amount of N-acetylhydroxyproline or N,O-diacetylhydroxyproline oleyl ester.

* * * * *